United States Patent [19]

Ferguson et al.

[11] Patent Number: 5,972,335
[45] Date of Patent: Oct. 26, 1999

[54] WOUND HEALING

[75] Inventors: Mark William James Ferguson, Stockport; Mamta Shah, Manchester, both of United Kingdom

[73] Assignee: The Victoria University of Manchester, Manchester, United Kingdom

[21] Appl. No.: 08/718,492

[22] PCT Filed: Mar. 29, 1995

[86] PCT No.: PCT/GB95/00704

§ 371 Date: Nov. 12, 1996

§ 102(e) Date: Nov. 12, 1996

[87] PCT Pub. No.: WO95/26203

PCT Pub. Date: Oct. 5, 1995

[30] Foreign Application Priority Data

Mar. 29, 1994 [GB] United Kingdom ............... 9406154
Dec. 9, 1994 [GB] United Kingdom ............... 9424898

[51] Int. Cl.[6] ............... A61K 39/395; C07K 16/18; C07K 16/22
[52] U.S. Cl. ............... 424/141.1; 530/395; 530/387.1; 530/388.1; 530/388.23; 530/389.2; 424/145.1; 424/158.1
[58] Field of Search ............... 424/145.1, 158.1, 424/141.1; 530/395, 387.1, 388.1, 388.23, 389.2

[56] References Cited

FOREIGN PATENT DOCUMENTS

| 0 282 317 A2 | 9/1988 | European Pat. Off. |
| 9217206 | 10/1992 | United Kingdom . |
| WO 91/04748 | 4/1991 | WIPO . |
| 92 17206 | 10/1992 | WIPO . |
| 93 10808 | 6/1993 | WIPO . |
| 93 19769 | 10/1993 | WIPO . |
| 93 19783 | 10/1993 | WIPO . |
| WO93/19769 | 10/1993 | WIPO . |
| WO 94/09812 | 5/1994 | WIPO . |
| WO9409812 | 5/1994 | WIPO . |

OTHER PUBLICATIONS

Shah et al: "Control of scarring in adult wounds by neutralizing antibody to transforming growth factor beta", The Llancet, vol. 339, No. 8787, Jan. 25, 1992, pp. 213 214.

Barcellos–Hoffet al: "Transforming growth factor–beta activation in irradiated murine mammary gland", The Journal Of Clinical Investigation, vol. 92, No.2 Feb. 1994, pp. 892–899.

Shah et al: "Neutralising antibody to TGF–betal, 2 reduces cutaneous scarring in adult rodent", Journal Of Cell Science, vol. 107, No. 5 May 1994, pp. 1137–1157.

Shah et al: "Neutralisation of TGG–betal and TGF–beta2 or exogenous addition of TGF–beta3 to cutaneous rat wounds reduces scarring", Journal Of Cell Science, vol. 108, No. 3, Mar. 1995, pp. 985–1002.

Adzick et al: "Cells, matrix, growth factors, and the surgeon", Annals Of Surgery, vol. 220, No.1,JUL. 1994, pp. 10–18.

*Primary Examiner*—Anthony C. Caputa
*Assistant Examiner*—Geetha P. Bansal
*Attorney, Agent, or Firm*—Nixon & Vanderhye P.C.

[57] ABSTRACT

The present invention concerns compositions for promoting the healing of wounds or fibrotic disorders comprising at least one agent specific to either a growth factor or a protein associated therewith in a system and which affects the quantity of active growth factor in the system, in combination with a pharmaceuticlly acceptable carrier, diuluent or excipient.

6 Claims, 5 Drawing Sheets

| Effect | Production capacity | Affinity | Target/Assay Sensitivity | Clearance Rate | $V_{on/off}$ of Establishing Equilibrium |
|---|---|---|---|---|---|
| Block | Low | High | Low | High | Rapid |
| Enhance | High | Low | High | Low | Slow |

Fig. 2

Neutralising Antibodies to TGF-ß $_{1,2}$

1) Anti-Scarring

- Apply early - high ratio Ab/TGF-ß
- High affinity
- Multiple epitope recognition 2) Enhance TGF-ß activity e.g. to accelerate wound healing

- Chapherone/bound resevoir
- Apply late - low ratio Ab/TGF-ß
- Low affinity
- Single epitope recognition

Experimental Model

Standard 1cm full thickness, linear incision wound down to and including the paniculus carnosus muscle.

Experimental Model

A: Control wound (unmanipulated)

B: Sham control (PBS)

C: Experimental wound 1 (control antibody)

D: Experimental wound 2 (neutralising antibody)

WOUND HEALING

The present invention concerns compositions for promoting the healing of wounds or fibrotic disorders.

At present there is a lack of compositions for treating wounds or fibrotic disorders.

By "wounds or fibrotic disorders" is meant any condition which may result in the formation of scar tissue. In particular, this includes the healing of skin wounds, the repair of tendon damage, the healing of crush injuries, the healing of central nervous system (CNS) injuries, conditions which result in the formation of scar tissue in the CNS, scar tissue formation resulting from strokes, and tissue adhesion, for example, as a result of injury or surgery (this may apply to e.g. tendon healing and abdominal strictures and adhesions). Examples of fibrotic disorders include pulmonary fibrosis, glomerulonephritis and cirrhois of the liver, in which TGF-$\beta_1$ has been implicated and proliferative vitreoretinopathy, in which TGF-$\beta_2$ has been implicated.

In particular, there is a lack of compositions for promoting the healing of wounds or fibrotic disorders with reduced scarring. Scar tissue formation, although providing mechanical strength to a healed wound, can be unsightly and may impair the function of the tissue.

This is particularly the case in wounds which result in scar tissue formation in the CNS, the scar tissue inhibiting the reconnection of severed or re-growing nerve ends, so significantly affecting their function.

There is also a lack of compositions for use in the treatment of chronic wounds, for example venous ulcers, diabetic ulcers and bed sores (decubitus ulcers), especially in the elderly and wheel chair bound patients. Such compositions may be extremely useful in patients where wound healing is either slow or in whom the wound healing process has not yet started. Such compositions may be used to "kick-start" wound healing and may then be used in combination with compositions (e.g. those of PCT/GB93/00586) which promote the healing of wounds or fibrotic disorders with reduced scarring. Hence not only may a chronic wound be healed, but it may be healed with reduced scarring.

WO 92/17206 discloses compositions for use in the treatment of wounds to inhibit scar tissue formation during healing, comprising an effective activity-inhibiting amount of a growth factor neutralising agent or agents specific against only fibrotic growth factors together with a pharmaceutically acceptable carrier.

WO 93/19769 discloses a healing composition containing at least one non-fibrotic growth factor in combination with a pharmaceutically acceptable carrier.

These publications disclose the use of antibodies to TGF-$\beta_1$, TGF-$\beta_2$ and PDGF; binding proteins which prevent TGF-$\beta_1$, TGF-$\beta_2$ and PDGF from binding to their receptors by binding to the proteins or their receptors; soluble forms of the growth factor receptor or the growth factor binding domains of the receptors; and antisense oligonucleotides or ribosymes which act to prevent fibrotic growth factor mRNA translation.

Surprising results have now been obtained by the present inventors using antibodies specific to growth factors and proteins associated therewith.

According to the present invention there is provided a composition for promoting the healing of wounds or fibrotic disorders comprising at least one agent specific to either a growth factor or a protein associated therewith in a system and which affects the quantity of active growth factor in the system, in combination with a pharmaceutically acceptable carrier, diluent or excipient.

By "agent" is meant any compound or molecule which is capable of affecting the quantity of active growth factor in a system. Such an agent may work by neutralising, activating or deactivating a growth factor, affecting its half-life or by causing a change in its production level.

By "system" is meant the system to which the composition is applied and as such is defined by both the nature of the wound or fibrotic disorder and by the method of application of the composition. For example, in the case of a surface skin wound to which a composition is topically applied, "system" means the surface skin wound, and in a CNS disorder which is treated by injection of a composition into the blood stream, "system" means the body as a whole, whereas in a CNS disorder which is treated by a localised injection of a composition into the CNS, "system" means the CNS, in particular the area to which the injection was localised.

By "active growth factor" and "active quantity of growth factor" is meant growth factor which can effect a response in its target cells At least one agent may comprise an antibody or a fragment or a derivative thereof which binds to a growth factor or protein associated therewith.

Such an antibody may be selected from any one of the group of a monoclonal, phage, polyclonal and genetically engineered antibody.

At least one agent may comprise an antibody fragment comprising only the active binding site.

At least one agent may be specific to a single epitope.

At least one agent may be specific to a non-fibrotic growth factor; such a growth factor may be selected from the group of FGF-1, FGF-2, FGF-7, EGF, TGF$\alpha$, IL-10, IL-12, IL-17, TGF-$\beta_3$ and IFN$\alpha$.

At least one agent may be specific to a fibrotic growth factor; such a growth factor may be selected from the group of TGF-$\beta_1$, TGF-$\beta_1$, PDGFAA, PDGFBB, PDGFAB, a member of the CTGF family, IL-1, IL-2, IL-8 and TFN$\alpha$.

A composition according to the present invention may promote the healing of chronic wounds or it may promote the healing of wounds with reduced scarring.

At least one agent may act to potentiate the quantity of an active growth factor. Hence the increased level of active endogenous growth factor so potentiated may act to promote the healing of a wound.

Such a composition according to the present invention may promote the healing of chronic wounds and comprise at least one agent which potentiates a fibrotic growth factor. It may comprise an antibody specific to a single epitope on a growth factor selected from either one of the group of TGF-$\beta_1$ and TGF-$\beta_2$.

The inventors have found that, surprisingly, antibodies specific to a single epitope of TGF-$\beta_1$ and TGF-$\beta_2$ can either have no effect on the growth factor or can cause a potentiation if the growth factor.

Obviously not all antibodies specific to a growth factor will act to potentiate it since many may act to neutralise it or to inhibit its activity or may even have no noticeable effect. However, standard laboratory techniques may be used in order to generate and test antibodies and isolate those which act to potentiate growth factors.

Such a potentiation of a growth factor was unexpected, although potentiation has previously been observed in different systems. Heremans et al. (Eur. J. Immunol., 1992, 22:2395–2401) and Martens et al. (Eur. J. Immunol., 1993, 23:2026–2029) showed the potentiation of the cytokine IL-6 by the injection of monoclonal antibodies specific to IL-6 into mice which had previously been injected with endotoxin in order to induce a generalised Schwartzman reaction (endotoxic shock).

The exact mechanism of potentiation remains unknown. However, the hypotheses put forward by the research teams to explain these results may be applied to the present inventors own findings. For example, they propose that if the affinity of the cytokine receptor for the cytokine is higher than that of the antibody, the cytokine may still be active despite its binding to the antibody.

Alternatively, the increased cytokine levels after administration of antibody may be due to delayed elimination or to increased production. Delayed elimination of endogenous cytokine might be brought about by complex formation of the cytokine with the antibody. Such antibodies may act as carriers of cytokines, preventing their elimination from the circulation, urine etc. Alternatively, or additionally, a cytokine may exert negative control over its own synthesis and/or release in vivo. Thus partial neutralisation or sequestration of the cytokine at the tissue level may depress release, resulting in higher production levels (illustrated in FIG. 1). Finally, low affinity antibodies to the active site of the growth factor (so called "neutralising antibodies") may be most effective as potentiating complexing agents as they protect the active site from degradation.

A composition according to the present invention may also comprise at least two agents each of which is specific to a single different epitope on a growth factor, such that individually the agents either have no effect or act to potentiate the active quantity of the growth factor, but which in combination act to reduce the active quantity of the growth factor, the reduced quantity of the active growth factor acting to promote the healing of a wound.

Such a composition may comprise two antibodies.

Such a composition amy be specific to a growth factor selected from one of the group of TGF-$\beta_1$ and TGF-$\beta_2$, the composition acting to promote the healing of a wound with reduced scarring.

Hence a composition according to the present invention may comprise two antibodies each of which is specific to a single different epitope on TGF-$\beta_1$, such that individually the antibodies either have no effect or act to potentiate the active quantity of TGF-$\beta_1$, but which in combination act to reduce the active quantity of TGF-$\beta_1$, the reduced quantity of the active growth factor acting to promote the healing of a wound.

Again the exact mechanism of this neutralisation is unknown. However, it is likely that recognition of two or more epitopes by two or more neutralising antibodies or fragments thereof results in the formation of a large enough antibody/growth factor complex for rapid detection and clearing by the body's systems (by kupfer cells of the liver), and hence neutralisation. By contrast the detection of a single epitope by a single antibody, or fragment thereof, may result in a small complex, not easily detected and hence either no effect or potentiation of the growth factor. Further, as summarised in FIGS. 2 and 3 the affinity of the antibody (low affinity for potentiation, high affinity for neutralisation) and ratio of antibody to growth factor (high for neutralisation, low for potentiation) etc. are likely to influence the end result. It follows that the same antibody may be used to achieve either neutralisation or potentiation according to circumstances and to whether it is coupled with another neutalising antibody recognising a different epitope. It further follows that genetically engineered antibodies or coupled antibodies or fragments thereof, e.g. diabodies capable of for example binding one or more epitope or fragments of larger complexes might also be used for the purposes of neutralisation.

A composition according to the present invention may comprise at least two agents specific to at least two growth factors, such that individually the agents either have no effect or have a slight neutralising effect upon the active quantity of their respective growth factors, but which in combination have a significantly greater neutralising effect upon the active quantity of their respective growth factors.

Such a composition may comprise two antibodies.

Such a composition may comprise two antibodies, one being specific to a single epitope on TGF-$\beta_1$ and which has a slight neutalising effect upon the active quantity of TGF-B$\beta_1$, and the other being specific to a single epitope on TGF-$\beta_2$ and which has no effect upon TGF-$\beta_2$, but which in combination act to reduce the active quantities of TGF-$\beta_1$ and TGF-$\beta_2$, thereby promoting the healing of wounds with reduced scarring.

The inventors have found that, surprisingly, a composition comprising two antibodies, one being a neutralising antibody specific to TGF-$\beta_1$ and the other being an antibody specific to TGF-$\beta_2$ but which has no effect on it, does not in fact give the expected results. Instead of the composition having a slight neutralising effect upon TGF-$\beta_1$ and no effect upon TGF-$\beta_2$, it was found that it actually had a significantly increased neutralising effect upon TGF-$\beta_1$ and TGF-$\beta_2$, the two antibodies although specific to different proteins apparently acting synergistically.

The blocking and potentiating properties of neutralising antibodies to TGF-$\beta_1$ and TGF-$\beta_2$ are summarised in FIGS. 2 and 3.

Alternatively, a composition according to the present invention may comprise an agent specific to a protein associated with a growth factor and which reduces the active quantity of the growth factor associated therewith.

Such a composition may act to promote the healing of wounds with reduced scarring and comprise an agent specific to the Latency Associated Peptide associated with either the latent TGF-$\beta_1$ or latent TGF-$\beta_2$ complex.

The inventors have found that, surprisingly, an antibody specific to the latency associated peptide which forms a art of the latent TGF-$\beta$ complex acts to affect a reduction in the quantity of active TGF-$\beta_1$.

The exact nature of the mechanism by which this reduction in the active quantity of TGF-$\beta_1$ is affected remains unknown, although the binding of the large latent TGF-$\beta$ complex to smooth muscle cells is blocked by the anti-LAP antibody (Sato et al., 1993, J. of Cell Biol., 123:1249–1254).

A composition according to the present invention may be used in conjunction with a composition which promotes the healing of wounds.

Such a composition which promotes the healing of wounds may promote the healing of wounds with reduced scarring.

Such a composition which promotes the healing of wounds with reduced scarring may comprise at least one non-fibrotic growth factor. At least one non-fibrotic growth factor may be selected from the group of FGF-1, FGF-2, FGF-7, EGF, TGF$\alpha$, IL-10 IL-12, IL-17, TGF-$\beta_3$ and IFN$\alpha$.

Thus the composition of the present invention may be used in combination with known compositions which promote the healing of wounds with reduced scarring. In particular, a composition according to the present invention which promotes the healing of chronic wounds may be used in a method whereby it is initially applied to the wound to "kick-start" wound healing, and then a composition which promotes the healing of wounds with reduced scarring may be used. Hence chronic wounds may not only be healed, but healed with reduced scarring.

A composition according to the present invention may be used in a method of treatment or diagnosis of the human or animal body.

Also provided is a method of treatment of the human or animal body comprising the use of a composition according to the present invention.

The invention will be further apparent from the following description, with reference to the several figures of the accompanying drawings. Of the figures, FIG. 1 shows a possible effect of antibodies upon cytokine levels;

FIGS. 2 and 3 show the effect of antibody affinity and ratio of antibody to growth factor upon growth factor activity;

EXPERIMENTAL PROCEDURE

Potentiation/Neutralisation of TGF-$\beta_1$ and TGF-$\beta_2$

Figure 1:
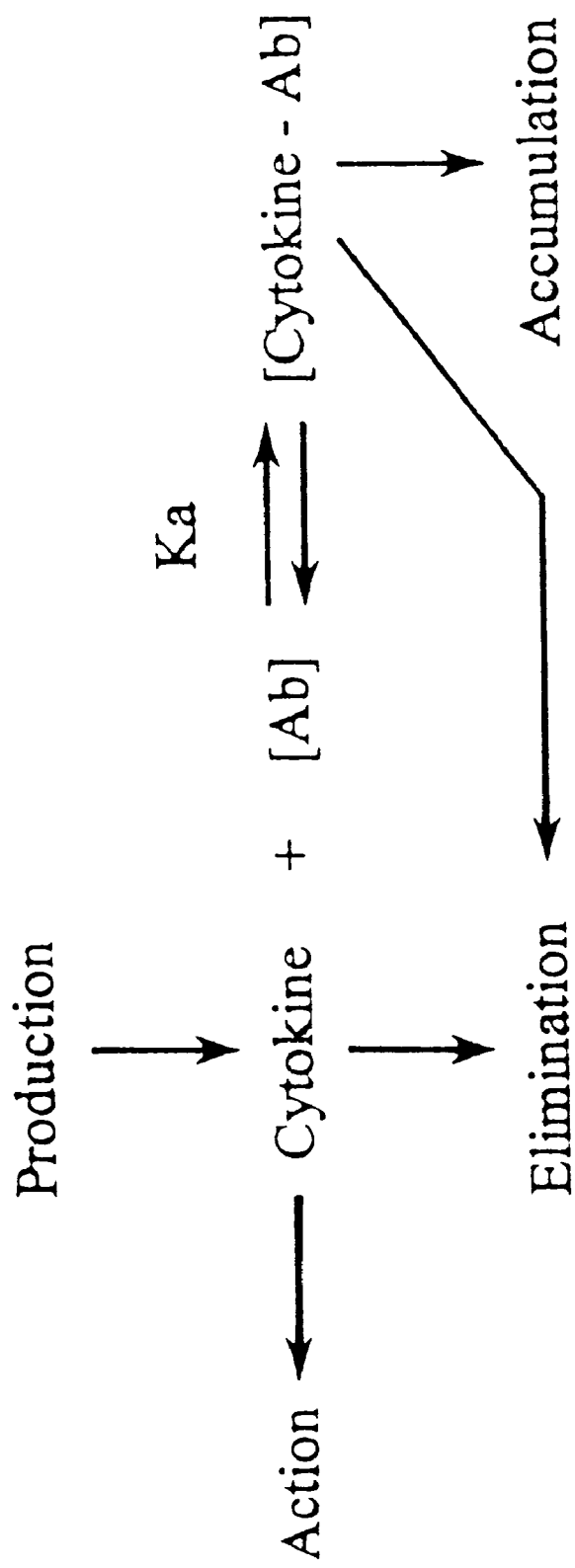
Figures 4A, 4B:
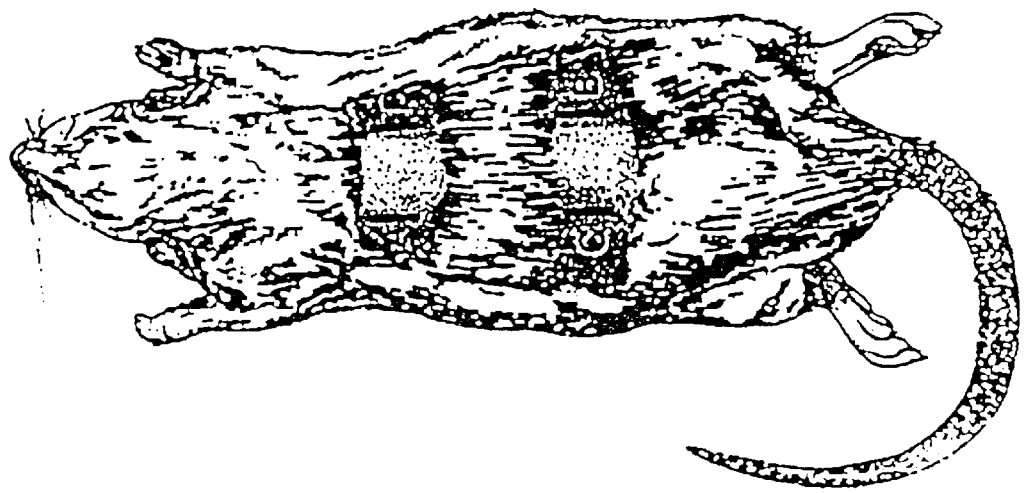
FIG. 4 shows the rat experimental model used for the potentiation/neutralisation experiments.
Figures 5A, 5B:
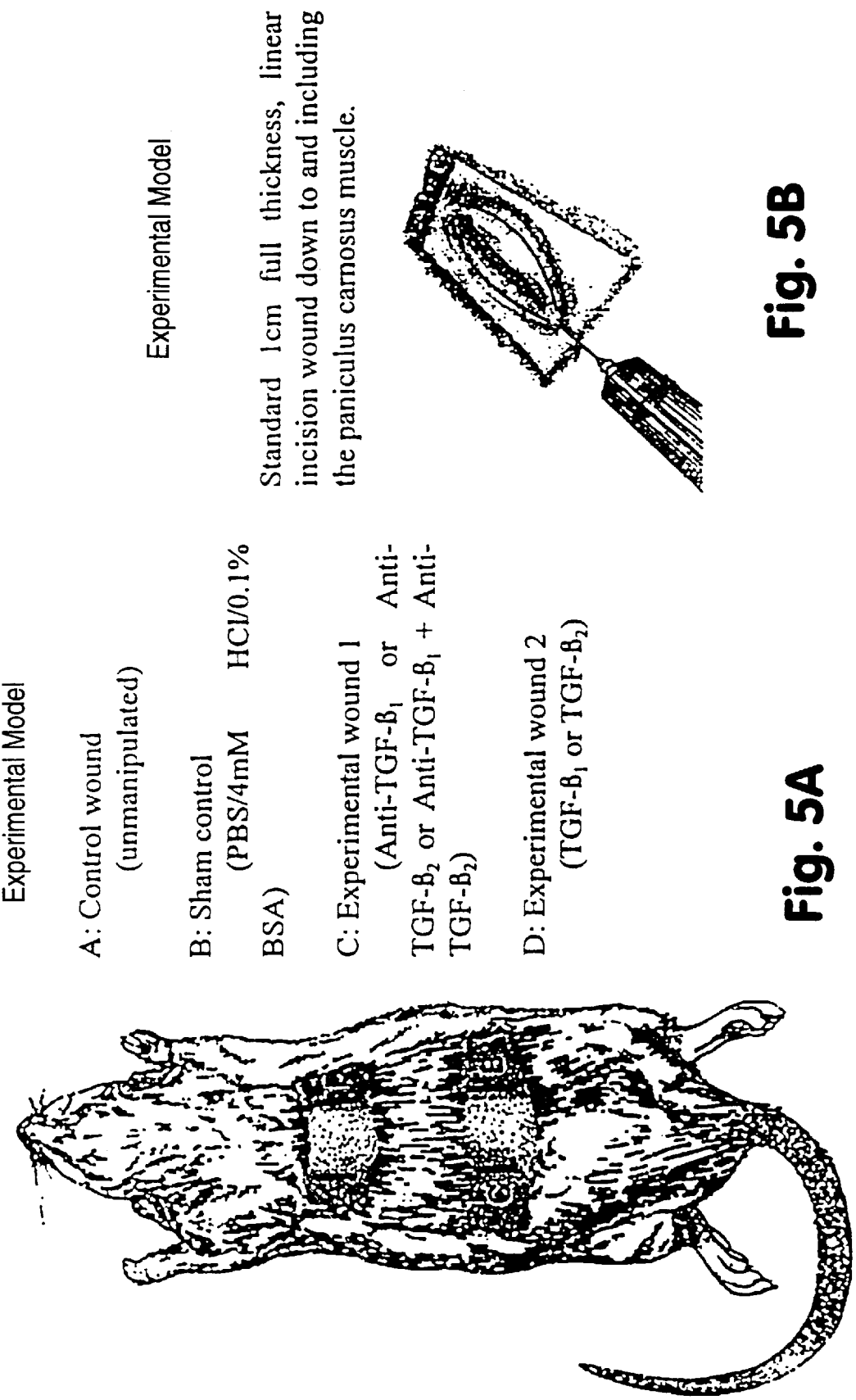
FIG. 5 shows the rat experimental model used for the Latency Associated peptide experiments.

Adult, male Sprague-Dawley rats (Charles River UK Ltd., Kent, UK) weighing 225–250 grammes were anaesthetised by halothane, nitrous oxide and oxygen inhalation. After locally clipping the fur, four full-thickness, linear incisions, 1 cm in length, down to and including the panniculus carnosus were made on the dorsal skin of the animal. The incisions were placed equidistant from the midline and adjacent to the four limbs (FIG. 4).

In each animal one of the wounds (control) was unmanipulated, one (sham-control) was injected with PBS/ 0.1% BSA/4 mM HCl (carrier used to make up the TGF-$\beta$ isoforms), one was injected with TGF-$\beta_1$, TGF-$\beta_2$ or TGF-$\beta_3$, and one was injected with neutralising antibody to TGF-$\beta_1$ alone, neutralising antibody to TGF-$\beta_2$ alone or a combination of neutralising antibodies to TGF-$\beta_1$ and TGF-$\beta_2$ (Table 1). The actual site of each treatment was rotated between the four wounds to control for anterior-posterior differences in the healing of rodent wounds. All injections were of 100 µl each and administered by local infiltration of the wound margins (inset in FIG. 4). The wounds were treated on days 0, 1 and 2 post-wounding. Animals were allowed to recover and housed in individual cages and fed normal rat chow and water ad libitum. Animals were killed by chloroform overdose on various days after wounding and the wounds harvested.

In order to determine the optimum doses of isoform specific neutralising antibodies to TGF-$\beta_1$ and TGF-$\beta_2$, dose response experiments were performed. Animals were divided into two groups: in group I, one of the wounds was treated with neutralising antibody to TGF-$\beta_1$ and one of the wounds with TGF-$\beta_1$; in group II, one of the wounds was treated with neutralising antibody to TGF-$\beta_2$ and one of the wounds with TGF-$\beta_2$.

The isoform specific neutralising antibodies and the TGF-$\beta$ isoforms used in these experiments were a gift from Dr. A. B. Roberts (Lab. of Chemoprevention, NIH, Bethesda, USA). These antibodies have been well characterised and the specificities established (Roberts, A. B. et al., 1990, Growth Factors, 3:277–286; Danielpour et al., In Growth Factors, 2:61, 1989).

16 animals per group were studied; wounds were analysed on days 7 and 14 post-wounding in each set of experiments.

TABLE 1 doses of TGF-$\beta$ isoforms and neutralising antibodies thereto.

| | Group I | | Group II | | Group III Anti-TGF-$\beta_1$ + Anti-TGF-$\beta_2$ | |
|---|---|---|---|---|---|---|
| Set | Anti-TGF-$\beta_1$ µl/injection | TGF-$\beta_1$ ng/inj | Anti-TGF-$\beta_2$ µl/inj | TGF-$\beta_2$ ng/inj | µl/inj (of each) | TGF-$\beta_3$ ng/inj |
| A | 0.01 | 0.1 | 0.01 | 0.1 | 0.01 | 0.1 |
| B | 0.1 | 1 | 0.1 | 1 | 0.1 | 1.0 |
| C | 1 | 10 | 1 | 10 | 1.0 | 10.0 |
| D | 5 | 50 | 5 | 50 | 5.0 | 50.0 |

(1 µl of Anti-TGF-$\beta_1$ neutralises approximately 4 ng of TGF-$\beta_1$ in vitro; 1 µl of Anti-TGF-$\beta_2$ neutralises approximately 6 ng TGF-$\beta_2$ in vitro. TGF-$\beta_1$ and TGF-$\beta_2$ were extravted from porcine platelets; TGF-$\beta_3$ was recombinant TGF-$\beta_3$ expressed in NIH 3T3 cells.)

After harvesting, the wounds were bissected, one half being frozen and processed for immunochemistry and the other half being fixed in 4% paraformaldehyde and processed for parrafin embedding.

Results

The results of this study showed that the exogenous addition of neutralising antibody to TGF-$\beta_1$ plus neutalising antibody to TGF-$\beta_2$ to incisional, cutaneous wounds in adult rodents reduces scarring. Neutralising antibody to TGF-$\beta_1$ plus neutralising antibody to TGF-$\beta_2$ reduced the monocyte and macrophage profile, neovascularisation, fibronectin, collagen III and collagen I deposition in the early stages of wound healing and improved the architecture of the neodermis, thereby reducing scarring. Exogenous addition of neutralising antibody to TGF-$\beta_1$ resulted in only a marginal reduction in scarring. By contrast, exogenous addition of neutralising antibody to TGF-$\beta_2$ to wounds did not alter scarring. None of the wounds showed delayed healing.

Full results and discussion of these experiments are published in the PhD Thesis of Mamta Shah, Cutaneous Scarring: Modulation by Transforming Growth Factor-Beta and its Antagonists, University of Manchester, 1993, Chapter 5.

Latency Associated Peptide

Two adult, male Sprague-Dawley rats were anaesthetised and their fur locally clipped to allow for four full-thickness linear incisions, 1 cm in length to be made on the dorsal skins of two adult male Sprague-Dawley rats. The incisions were made to include the panniculus carnosus and were placed equidistant from the midline and adjacent to the four limbs.

In each of the animals, one of the wounds was injected with control antibody, one was injected with phosphate buffered saline (the carrier of the antibodies), one remained unmanipulated and one was injected with neutralising antibody to the Latency Associated Peptide (LAP) associated with the Large Latent TGF-$\beta_1$ complex. All injections were of 100 µl each and were administered by local dermal infiltration of the wound margins. Animals were allowed to recover and housed in individual cages and fed normal rat feed and water ad libitum. Animals were killed by chloroform overdose on various days after wounding and the wounds harvested.

The first animal was treated with a dose of 50 µg of antibody per wound, administered by a single injection at the time of wounding. This animal was killed seven days post-wounding and the wounds removed and processed for histological examination.

The second animal was treated with a dose of 100 µg per wound of neutalising antibody. This animal was killed forty days post-wounding. Wounds were removed and processed for histological examination. Histological examination involved staining using connective tissue stains, e.g. mallory, to highlight collagen, orientation and organisation within the wound site.

Results

Histological examination of the first animal at seven days post-wounding revealed very few differences between wounds treated with the neutralising antibody and the control wounds. There was, however, limited evidence of reduced collagen in the wounds treated with the neutralising antibody.

Histological examination of the second animal revealed a marked improvement in wound quality (scarring) at forty days post-wounding in the wounds treated with 100 µg of neutralising antibody. Staining showed that the collagen fibres in the wound were thicker and organised in a "basketweave" fashion more reminiscent of normal dermis. Indeed, one wound was extremely difficult to distinguish from the normal dermis in the papillary layers of the dermis, mild disorganisation only being noticed in the reticular layers of the dermis and the cut panniculus carnosus.

Hence antibodies specific to proteins associated with fibrotic growth factors, and particularly neutralising antibodies specific to the Latency Associated Peptide (LAP) associated with the Large Latent TGF-$\beta_1$ complex, are able to promote the healing of wounds with reduced scar tissue formation.

The invention is further defined by the following claims wherein we claim:

1. A composition comprising at least two antibodies, a first of said antibodies being specific for a single epitope on TGF-$\beta_1$ and a second of said antibodies being specific for a single epitope on TGF-$\beta_2$, said first of said antibodies, individually, having a neutralizing effect upon the activity of TGF-$\beta_1$ and said second of said antibodies, individually, having no neutralizing effect on the activity of TGF-$\beta_2$, wherein, in combination, said at least two antibodies have a greater neutralizing effect upon the activity of TGF-$\beta_1$ and TGF-$\beta_2$ than that of said first antibody.

2. A composition comprising an antibody specific to a Latency Associated Peptide component of latent TGF-$\beta_1$ or of latent TGF-$\beta_2$, together with a pharmaceutically acceptable carrier therefor.

3. A composition comprising at least two antibodies each of which is specific for a single different epitope on a single fibrotic growth factor, such that individually the antibodies either have no effect on or act to potentiate the activity of the growth factor, but which in combination act to reduce the activity of the growth factor.

4. A composition according to claim 3, wherein the growth factor is selected from the group consisting of TGF-$\beta_1$ and TGF-$\beta_2$.

5. A method of promoting the healing of a wound with reduced scarring which comprises administering to a patient in need thereof an amount of the composition according to claim 1, 2, or 3 sufficient to promote said healing with reduced scarring.

6. A method of inhibiting fibrosis comprising administering to a patient in need thereof an amount of the composition according to claim 1, 2 or 3 sufficient to effect said inhibition.

* * * * *